US005514338A

United States Patent [19]

Simon et al.

[11] Patent Number: 5,514,338
[45] Date of Patent: May 7, 1996

[54] DEVICE FOR SENSING LIQUID HYDROCARBON

[75] Inventors: Morris Simon; Jay S. Simon, Northbrook, both of Ill.

[73] Assignee: One Plus Corp., Northbrook, Ill.

[21] Appl. No.: 345,998

[22] Filed: Nov. 29, 1994

[51] Int. Cl.$^6$ .................................................. G01N 27/12
[52] U.S. Cl. ................ 422/82.02; 422/68.1; 422/82.01; 422/88; 422/98; 73/61.51; 340/605; 340/620; 340/623
[58] Field of Search ............................. 422/68.1, 82.01, 422/82.02, 88, 98; 73/61.51; 340/605, 620, 623

[56]  References Cited

U.S. PATENT DOCUMENTS

| | | |
|---|---|---|
| 2,691,134 | 10/1954 | Ford . |
| 3,045,198 | 7/1962 | Dolan et al. . |
| 3,967,256 | 6/1976 | Galatis ................................. 340/605 |
| 3,970,863 | 7/1976 | Kishikawa et al. ................... 340/605 |
| 4,129,030 | 12/1978 | Dolan .................................. 73/31.05 |
| 4,206,402 | 6/1980 | Ishido .................................. 340/605 |
| 4,224,595 | 9/1980 | Dolan .................................... 422/88 |
| 4,237,721 | 12/1980 | Dolan .................................. 73/31.05 |
| 4,351,642 | 9/1982 | Bonavent et al. ................ 422/68.1 X |
| 4,384,477 | 5/1983 | Perry ................................... 73/61.51 |
| 4,549,171 | 10/1985 | Alciba et al. ........................ 340/605 |
| 4,563,741 | 1/1986 | Kobayashi ........................... 340/620 |
| 4,631,952 | 12/1986 | Donaghey .............................. 338/34 |
| 4,663,614 | 5/1987 | Rauchwerger ....................... 340/605 |
| 4,885,706 | 8/1989 | Hauptly ................................. 338/34 |
| 4,894,166 | 1/1990 | Pitts ..................................... 210/663 |
| 4,926,165 | 5/1990 | Lahlouh et al. ................. 340/605 X |
| 5,079,944 | 1/1992 | Boenning et al. .................... 73/23.4 |
| 5,109,202 | 4/1992 | Akiba ................................... 340/605 |
| 5,256,574 | 10/1993 | Neuberger et al. .................. 436/143 |
| 5,264,368 | 11/1993 | Clarke et al. .................. 427/68.1 X |

OTHER PUBLICATIONS

Leak edge brochure, "Underwriters Laboratories Certified Third Party E.P.A. Performance Specs. Reports," Dec. 12, 1991, cover sheet and pp. 1, 2, and 26.
Thirten pages of realted data, Dec. 18, 1991.
Letter data Dec. 17, 1991, Underwriters Laboratories to One Plus Corp., two pages.
One Plus Corp., "Leak–edge" brochure, Liquid Phase Hydrocarbon leak Detection Systems, front and back (undated).
One Plus Corp., "Leak–edge" brochure, "How it works", two pages (undated).
PetroSorb literature, six pages (undated).

*Primary Examiner*—Robert J. Warden
*Assistant Examiner*—Arlen Soderquist
*Attorney, Agent, or Firm*—Dressler, Goldsmith, Shore & Milnamow, Ltd.

[57]  ABSTRACT

A device is disclosed for sensing any of a wide range of liquid hydrocarbons. A ribbon-like sensor is employed, which has an inner, silicone rubber layer and an outer, silicone rubber layer and which has two broad faces and two narrow edges. The silicone rubber layers are capable of absorbing and swelling in the presence of a liquid hydrocarbon. The inner layer but not the outer layer is filled with electrically conductive particles, preferably carbon black particles, so as to be capable of switching from having an electrical impedance which is relatively low to having an electrical impedance which is relatively high when swollen in the presence of a liquid hydrocarbon. As made from an open cell, polyethylene foam, a porous body is attached to the sensor. The porous body is capable of floating with the sensor on water or on a liquid hydrocarbon and of conducting a liquid hydrocarbon through the porous body to the sensor. In one contemplated embodiment, the sensor is ribbon-like with two broad faces and two narrow edges, and the porous body comprises two porous slabs attached to the sensor, each porous slab covering one of the broad faces and extending beyond both of the narrow edges. The sensor may be usefully deployed in a serpentine arrangement between the porous slabs. The porous body may be alternatively wrapped around the sensor.

10 Claims, 2 Drawing Sheets

5,514,338

DEVICE FOR SENSING LIQUID HYDROCARBON

TECHNICAL FIELD OF THE INVENTION

This invention pertains to a device for sensing a liquid hydrocarbon. A sensor of a known type is employed, which has an electrically conductive layer capable of switching from a state of relatively low electrical impedance to a state of relatively high electrical impedance in the presence of a liquid hydrocarbon. A porous body attached to the sensor is made from a hydrophobic, polymeric material capable of conducting a liquid hydrocarbon through the porous body to the sensor.

BACKGROUND OF THE INVENTION

As early as Ford U.S. Pat. No. 2,691,134, it has been known to sense a liquid hydrocarbon, such as gasoline, by means of a sensor of a type comprising a rubber strip having carbon black particles dispersed therethrough so as to be capable of switching from a state of relatively low electrical impedance to a state of relatively high electrical impedance in the presence of a liquid hydrocarbon. The rubber strip absorbs the liquid hydrocarbon and swells in the presence of the absorbed hydrocarbon.

A sensor of the type noted above is available commercially from One Plus Corp. of Northbrook, Ill., under its LEAK EDGE trademark. The commercially available sensor has an inner, electrically conductive layer and an outer, electrically insulative layer. Each of the inner and outer layers is made from a silicone rubber, which is capable of absorbing any of a wide range of liquid hydrocarbons and swelling in the presence of the absorbed hydrocarbon. The inner layer but not the outer layer has carbon black particles dispersed therethrough so as to be capable of switching from a state of relatively low electrical impedance to a state of relatively high electrical impedance when swollen in the presence of a liquid hydrocarbon. Being electrically insulative, the outer layer prevents short circuiting of the sensor in water.

Since the sensor described in the preceding paragraph does not float on water or other liquids of low viscosity, its utility is limited in sewers, marine bilges, and other locations where water tends to flow so as to wash a liquid hydrocarbon from such a sensor or where liquids tend to accumulate at varying depths. This invention has resulted from efforts to enhance the utility of a sensor of the type noted above.

Sensors of related interest are disclosed in Dolan et al. U.S. Pat. No. 3,045,198, Kishikawa et al. U.S. Pat. No. 3,970,863, Dolan U.S. Pat. No. 4,129,030, Dolan U.S. Pat. No. 4,224,595, Dolan U.S. Pat. No. 4,237,721, Donaghey U.S. Pat. No. 4,631,952, Hauptly U.S. Pat. No. 4,885,706, Akiba U.S. Pat. No. 5,109,202, and Neuburger U.S. Pat. No. 5,256,574.

SUMMARY OF THE INVENTION

This invention provides, for sensing a liquid hydrocarbon, a device comprising a sensor of the type noted above and a porous body, which is attached to the sensor, and which is made from a hydrophobic, polymeric material capable of conducting the liquid hydrocarbon through the porous body to the sensor.

Being of the type noted above, the sensor has an inner, electrically conductive layer and an outer, electrically insulative layer. Each layer is made from a hydrophobic, polymeric material, which is capable of absorbing a liquid hydrocarbon and swelling in the presence of the absorbed hydrocarbon. Also, the inner layer but not the outer layer has electrically conductive particles dispersed therethrough so as to be capable of switching from a state of relatively low electrical impedance to a state of relatively high electrical impedance when swollen in the presence of a liquid hydrocarbon.

Generally, the porous body is capable of floating with the sensor on water or on a liquid hydrocarbon, whereby the utility of the sensor is enhanced in sewers, marine bilges, and other locations where water tends to flow so as to wash a liquid hydrocarbon from such a sensor or where liquids tend to accumulate at varying depths.

The porous body may be advantageously made from an open cell foam, such as an open cell, polyolefinic foam. Preferably, the porous body is made from an open cell, polyethylene foam.

Preferably, the sensor is ribbon-like with two broad faces and two narrow edges, and the porous body comprises two porous slabs attached to the sensor. Also, each slab may cover one of the broad faces and may extend beyond at least one of the narrow edges, preferably beyond both of the narrow edges. Moreover, the sensor may be usefully deployed in a serpentine arrangement between the porous slabs.

In a preferred embodiment, the sensor is similar to the commercially available sensor described above. Thus, each of the inner and outer layers is made from a silicone rubber, which is capable of absorbing a liquid hydrocarbon and swelling in the presence of the absorbed hydrocarbon. Also, the inner layer but not the outer layer has carbon black particles dispersed therethrough so as to be capable of switching from a state of relatively low electrical impedance to a state of relatively high electrical impedance when swollen in the presence of a liquid hydrocarbon. In the preferred embodiment, the porous body attached to the sensor is made from an open cell, polyethylene foam.

In one contemplated embodiment, in which the sensor is ribbon-like, the porous body is wrapped around the sensor in a generally tubular configuration. Moreover, the porous body is held in the generally tubular configuration, as by a reticular sleeve.

These and other objects, features, and advantages of this invention are evident from the following description of two contemplated embodiments of this invention with reference to the accompanying drawings.

DETAILED DESCRIPTION OF THE ILLUSTRATED EMBODIMENTS

Figure 1:
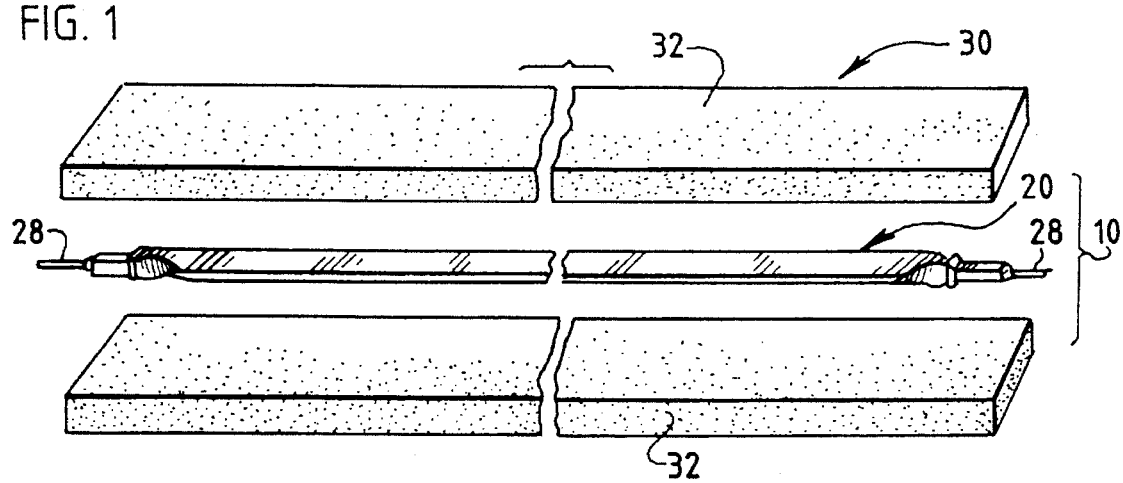
FIG. 1 is an exploded, perspective view of a device according to a preferred embodiment of this invention and useful for sensing a liquid hydrocarbon.
Figure 2:
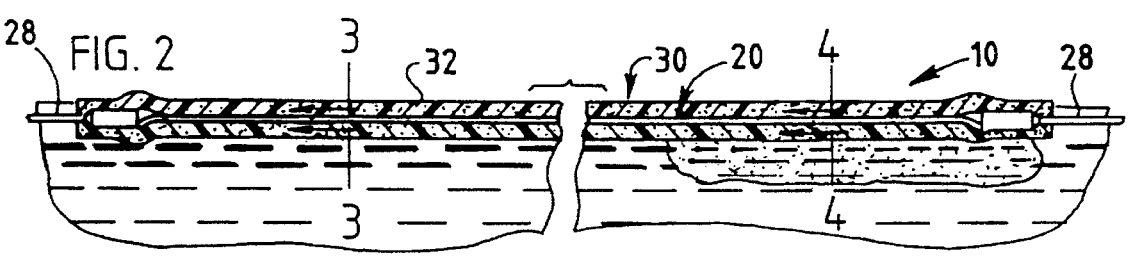
FIG. 2 is a longitudinal, sectional view taken in a vertical plane to show the same device floating on a body of water with a floating mass of gasoline, as an example of a liquid hydrocarbon that such a device is capable of sensing.
Figure 3:
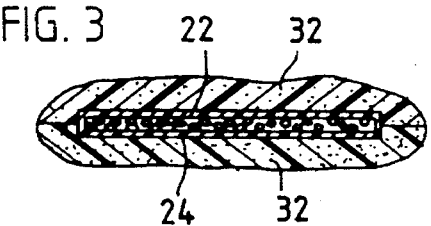
FIG. 3, on an somewhat enlarged scale, is a sectional view taken along line 3—3 of FIG. 2, in a direction indicated by arrows.
Figure 4:
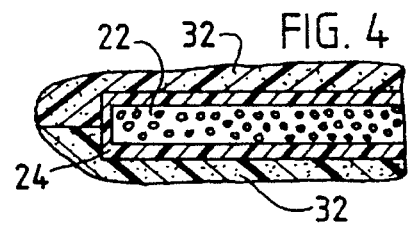
FIG. 4, on a further enlarged scale, is a sectional view taken along line 4—4 of FIG. 2, in a direction indicated by arrows.

As illustrated in FIGS. 1 through 4, a device 10 according to a preferred embodiment of this invention and useful for sensing a liquid hydrocarbon comprises a sensor 20 of the type noted above and a porous body 30, which comprises two porous slabs 32. The sensor 20 is ribbon-like with two broad faces and two narrow edges. The porous slabs 32, which are thin, narrow, and elongate, are attached to each other and to the sensor 20 so as to cover the broad faces and so as to extend beyond both of the narrow edges. The sensor 20 is deployed in a linear arrangement. The porous slabs 32 may be adhesively attached to each other, at discrete locations, with the sensor 20 disposed between the porous slabs 32 so as to be frictionally retained therebetween or may be alternatively fastened together by fasteners (not shown) or stitching (not shown) with the sensor 20 disposed therebetween so as be frictionally retained therebetween. Also, the porous slabs 32 may be adhesively attached to the sensor 20, at discrete locations.

Preferably, and as illustrated, the sensor 20 is similar to the commercially available sensor described above. Thus, the sensor 20 has an inner, electrically conductive layer 22 and an outer, electrically insulative layer 24. Each of these layers 22, 24, is made from a hydrophobic, polymeric material, preferably a silicone rubber, which is capable of absorbing any of the wide range of liquid hydrocarbons and swelling in the presence of the absorbed hydrocarbon. The inner layer 22 but not the outer layer 24 is provided with electrically conductive particles 26, preferably carbon black particles, which are dispersed therethrough so as to be capable of switching from a state of relatively low electrical impedance to a state of relatively high electrical impedance when swollen in the presence of any of the wide range of liquid hydrocarbons. Being electrically insulative, the outer layer 24 prevents short circuiting of the sensor 20 in water.

Also, at each end of the sensor 20, the inner layer 22 is terminated with an electrical connector 28. The electrical connectors 28 are connected to suitable instrumentation (not shown) for determining when the inner layer 22 has switched from the state of relatively low electrical impedance to the state of relatively high electrical impedance. Instrumentation available commercially from One Plus Corp., supra, for use with the commercially available sensor described above is suitable.

Preferably, each of the porous slabs 32 of the porous body 30 is made from an open cell, cross-linked, polyethylene foam, which is available commercially from PetroSorb, Inc. of Everett, Wash., under its PETROSORB trademark. As made from such a foam, the porous body 30 is hydrophobic but is capable of absorbing many times its weight in any of a wide range of liquid hydrocarbons. Moreover, the porous body 30 is capable of conducting the absorbed hydrocarbon through the porous body 30 to the sensor 20, via capillary action. If pressed, washed, and dried, the porous body 30 is reusable.

Figure 5:
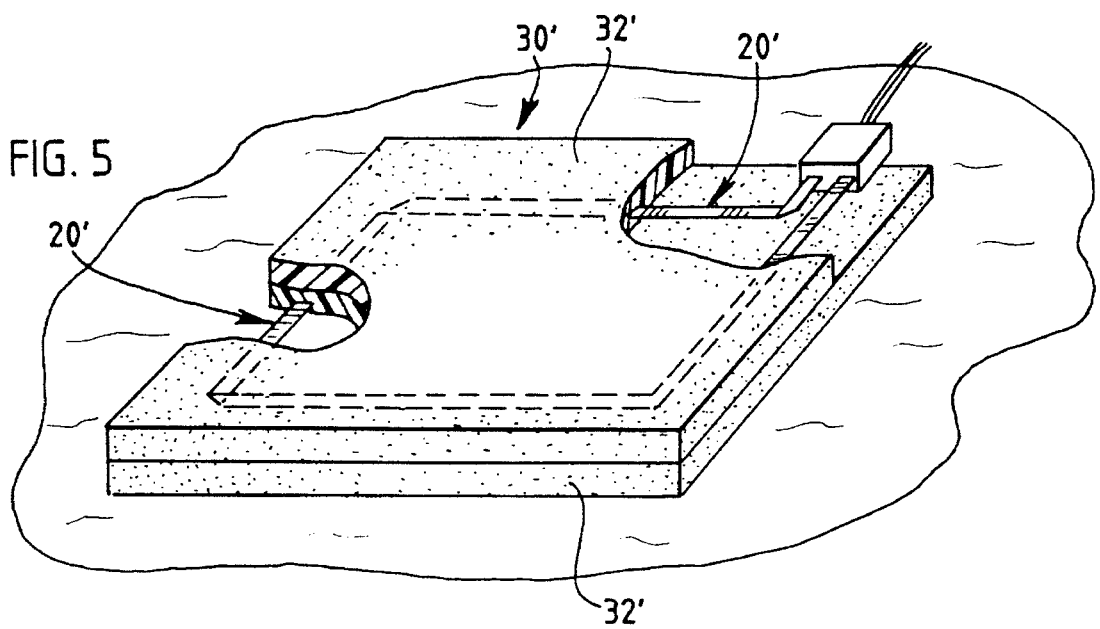
FIG. 5 is a partly fragmentary, perspective view of a device according to an alternative embodiment of this invention and useful for sensing a liquid hydrocarbon, the device being shown as floating on a body of water.

As illustrated in FIG. 5, a device 10' according to an alternative embodiment of this invention and useful for sensing a liquid hydrocarbon comprises a sensor 20' of the type noted above and a porous body 30', which comprises two porous slabs 32'. Being similar to the sensor 20, the sensor 20' is ribbon-like with two broad faces and two narrow edges. The porous body 30' comprises two porous slabs 32', which are thin, square, but similar otherwise to the porous slabs 32, and which are attached to each other and to the sensor 20' so as to cover the broad faces and so as to extend beyond both of the narrow edges. The sensor 20' is folded onto itself at discrete locations, as and where illustrated, and is deployed in a serpentine arrangement between the porous slabs 32'. The porous slabs 32' may be adhesively attached to each other, at discrete locations, with the sensor 20' disposed between the porous slabs 32' so as to be frictionally retained therebetween or may be alternatively fastened together by fasteners (not shown) or stitching (not shown) with the sensor 20' disposed therebetween so as be frictionally retained therebetween. Also, the porous slabs 32' may be adhesively attached to the sensor 20', at discrete locations.

Figure 6:
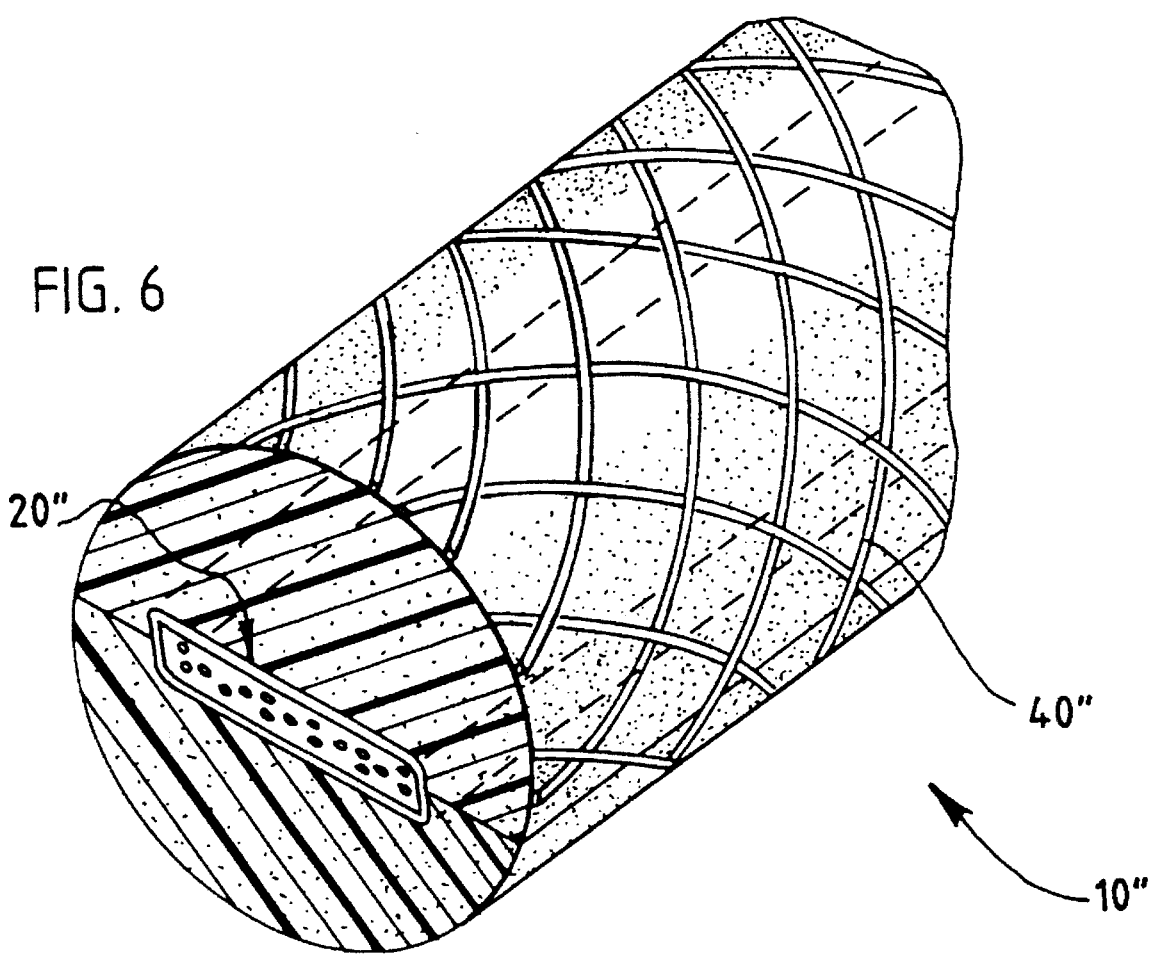
FIG. 6 is a perspective, cross-sectional view of a device according to another alternative embodiment of this invention and useful for sensing a liquid hydrocarbon.

As illustrated in FIG. 6, a device 10" according to another alternative embodiment of this invention and useful for sensing a liquid hydrocarbon comprises a sensor 20" of the type noted above and a porous body 30". Being similar to the sensor 20, the sensor 20" is ribbon-like. Being wider than one of the porous slabs 32, the porous body 30" is wrapped around the sensor 20" in a generally tubular configuration, in which the porous body 30" is held. As shown, the porous body 30" is held in the tubular configuration by a reticular sleeve 40" of a suitable netting material, such as nylon.

In any of the devices illustrated in the drawings and described above, because the porous body is capable of floating with the sensor on water or on any of the wide range of liquid hydrocarbons that float on water, the porous body is capable of absorbing the hydrocarbon liquid and conducting the liquid hydrocarbon through the porous body to the sensor, even in a sewer, marine bilge, or other location where liquids tend to flow or where liquids tend to accumulate at varying depths.

The devices illustrated in the drawings and described above are useful for sensing any of a wide range of liquid hydrocarbons including alkanes, alkenes, aromatic hydrocarbons, chlorinated hydrocarbons, alcohols, ethers, organic acids, esters, ketones, and aldehydes. Other liquid hydrocarbons that can be so sensed include thiophene, carbon disulfide, dimethyl solfoxide, pyridine, pyrrole, vinyl pyridine, vinyl pyrrolidone, and dimethylformamide, as well as gasoline, natural gas liquids ($C_6$ to $C_{16}$), napthas, kerosene, jet fuels, and crude oil.

Examples of alkanes that can be so sensed are pentane, hexane, cyclohexane, heptane, octane, decane, and dodecane. Examples of alkenes that can be so sensed are butadiene, isoprene, hexene, and octene. Examples of aromatic hydrocarbons that can be so sensed include benzene, toluene, xlyene, cumene, styrene, vinyl toluene, dodecyl benzene, and nonyl benzene. Examples of chlorinated hydrocarbons that can be so sensed include methylene chloride, chloroform, carbon tetrachloride, trichloroethane, ethylene dichloride, vinyl chloride monomer, chlorobenzene, and chlorofluorocarbons. Examples of alcohols that can be so sensed include methly, butyl, amyl, and allyl alcohols. Examples of ethers that can be so sensed include diethyl ether, methly isobutyl ether, tetrahydrofuran, and methyl tertiary butyl ether. Examples of organic acids that can be so sensed include acetic acid, formic acid, butanoic acid, acrylic acid, and phenol. Examples of esters that can be so sensed include ethyl acrylate, ethyl butyrate, butyl acetate, amyl acetate, dibutyl phthalate, dioctyl phthalate, and carbitol acetate. Examples of ketones that can be so sensed include methyl isobutyl ketone, cyclohexanone, i-phorone, acetone, and methyl ethyl ketone. Examples of aldehydes that can be so sensed include butyraldehyde and benzaldehyde.

Various modifications may be made in the illustrated embodiments described above without departing from the scope and spirit of this invention.

We claim:

1. For sensing a liquid hydrocarbon, a device consisting essentially of a sensor having an inner, electrically conductive layer and an outer, electrically insulative layer, each layer being made from a hydrophobic, polymeric material capable of absorbing a liquid hydrocarbon and swelling in the presence of the absorbed hydrocarbon, the inner layer but not the outer layer having electrically conductive particles dispersed therethrough for switching from a state of relatively low electrical impedance to a state of relatively high electrical impedance when swollen in the presence of a liquid hydrocarbon, and a porous body attached to and contacting the outer layer of the sensor, the porous body being made from a hydrophobic, cellular, polymeric material for absorbing a liquid hydrocarbon and conducting the absorbed hydrocarbon through the porous body to the sensor.

2. The device of claim 1 wherein the porous body is capable of floating with the sensor on water or on a liquid hydrocarbon.

3. The device of claim 1 wherein the porous body is made from an open cell foam.

4. The device of claim 1 wherein the porous body is made from a open cell, polyolefinic foam.

5. The device of claim 1 wherein the porous body is made from an open cell, polyethylene foam.

6. The device of claim 1 wherein the sensor is ribbon-shaped with two broad faces and two narrow edges and wherein the porous body comprises two porous slabs attached to the sensor, each slab covering one of the broad faces and extending beyond at least one of the narrow edges.

7. The device of claim 1 wherein the sensor is ribbon-shaped with two broad faces and two narrow edges and wherein the porous body comprises two porous slabs attached to the sensor, each porous slab covering one of the broad faces and extending beyond both of the narrow edges.

8. The device of claim 7 wherein the sensor is deployed in a serpentine arrangement between the porous slabs.

9. For sensing a liquid hydrocarbon, a device comprising a ribbon-shaped sensor having an inner, electrically conductive layer and an outer, electrically insulative layer, each layer being made from a hydrophobic, polymeric material capable of absorbing a liquid hydrocarbon and swelling in the presence of the absorbed hydrocarbon, the inner layer but not the outer layer having electrically conductive particles dispersed therethrough for switching from a state of relatively low electrical impedance to a state of relatively high electrical impedance when swollen in the presence of a liquid hydrocarbon, and a porous body attached to and contacting the outer layer of the sensor, the porous body being made from a hydrophobic, cellular, polymeric material for conducting a liquid hydrocarbon through the porous body to the sensor, the porous body being wrapped around the sensor in a generally tubular configuration, in which the porous body is held.

10. The device of claim 9 wherein the porous body is held in the generally tubular configuration by a reticular sleeve.

* * * * *

UNITED STATES PATENT AND TRADEMARK OFFICE
CERTIFICATE OF CORRECTION

PATENT NO. : 5,514,338

DATED : May 7, 1996

INVENTOR(S) : Simon et al.

It is certified that error appears in the above-indentified patent and that said Letters Patent is hereby corrected as shown below:

On title page, under "References Cited"
(11th line) Cited Patent 4,549,171 was invented by --Akiba et al.--, not "Alciba et al.".

Column 2, line 59, "an" should be --a--.

Column 4, line 16, after "as", --to-- should be inserted.

Column 5, line 32 (CLAIM 4), "a open cell" should be --an open cell--.

Signed and Sealed this

Fifth Day of November, 1996

Attest:

BRUCE LEHMAN

*Attesting Officer*  *Commissioner of Patents and Trademarks*